United States Patent [19]
Dai et al.

[11] Patent Number: 5,476,972
[45] Date of Patent: Dec. 19, 1995

[54] ISOPROPYL ALCOHOL AND ETHER PRODUCTION FROM CRUDE BY-PRODUCT ACETONE

[75] Inventors: Pei-Shing E. Dai; Robert J. Taylor, Jr., both of Port Arthur; John F. Knifton, Austin; Bobby R. Martin, Beaumont, all of Tex.

[73] Assignee: Texaco Chemical Inc., White Plains, N.Y.

[21] Appl. No.: 188,007

[22] Filed: Jan. 28, 1994

[51] Int. Cl.⁶ ........................................ C07C 41/09
[52] U.S. Cl. ........................ 568/671; 568/698; 568/881; 568/883
[58] Field of Search ............................. 568/881, 883, 568/698, 671

[56] References Cited

U.S. PATENT DOCUMENTS

| | | | |
|---|---|---|---|
| 4,459,419 | 7/1984 | Seemuth | 568/881 |
| 5,313,006 | 5/1994 | Knifton | 568/698 |

OTHER PUBLICATIONS

Verzele et al, J.C.S. (1963) pp. 5598–5600.

Primary Examiner—Johann Richter
Assistant Examiner—John Peabody
Attorney, Agent, or Firm—James L. Bailey; Kenneth R. Priem; Cynthia L. Hunter

[57] ABSTRACT

Disclosed is a one-step method for synthesis of ethers from mixtures of acetone and t-butyl alcohol which comprises reacting an acetone-rich feed over a bifunctional catalyst comprising 5%–45% by weight hydrogenation catalyst on 55%–95% of the total catalyst weight of a support comprising a zeolite and a Group III or IV oxide.

15 Claims, 1 Drawing Sheet

1

ISOPROPYL ALCOHOL AND ETHER PRODUCTION FROM CRUDE BY-PRODUCT ACETONE

CROSS-REFERENCE

This application is related to U.S. Ser. Nos. 08/096,873 now abandoned; 08/057,373 now abandoned; and U.S. application Ser. No. 08/148,248 now U.S. Pat. No. 5,364,981. It is also related to U.S. Pat. Nos. 4,822,921; 4,827,048; 5,099,072; 5,081,318; 5,059,725; 5,157,162; 5,162,592; 5,157,161; 5,183,947; and allowed U.S. Ser. Nos. 07/917,218; 07/878,121; and 07/917,885, all of which are incorporated by reference herein in their entirety.

FIELD OF THE INVENTION

This invention concerns a novel one-step integrated procedure for production of high octane blending components for reformulated gasoline from a crude by-product acetone stream which comprises reacting the crude acetone stream over a bifunctional catalyst to give an effluent-rich in diisopropyl ether (DIPE), methyl t-butyl ether (MTBE) and isopropyl t-butyl ether (IPTBE). The bifunctional (hydrogenation/etherification) catalyst comprises a hydrogenation catalyst on a support comprising a zeolite from the group consisting of β-zeolite, a medium-pore pentasil and Y-zeolite and an oxide from Group III or IV of the Periodic Table.

BACKGROUND OF THE INVENTION

It is known to those skilled in the art that ethers, including both symmetrical and unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Hydrogenation catalysts are known and are generally selected from Group VIII of the Periodic Table. Suitable metals include, but are not limited to, platinum, palladium, tin, nickel and copper alone, or in combination.

In U.S. Pat. No. 3,955,939 to Sommer et al. (1976), there is disclosed the production of a water-free mixture of isopropyl alcohol, diisopropyl alcohol, diisopropyl ether and by-products by the catalytic hydration of propylene in the gaseous phase at temperatures of 140°–170° C., wherein the water-free mixture formed according to the process can be used directly as an additive to gasoline fuel.

Conversion of acetone to MIBK is addressed in U.S. Pat. No. 3,953,517. The catalyst is a noble metal. In U.S. Pat. No. 5,059,724 a method is disclosed for the selective production of methyl isobutyl ketone.

In U.S. Pat. No. 5,017,729 there is disclosed a multistage process for producing phenol, wherein acetone is hydrogenated in the fourth step.

The use of zeolites for certain reactions is known in the art. β-zeolite was first synthesized at Mobil R&D labs and exhibited improved thermal and acid stability over previously synthesized zeolites.

One of the earliest disclosures of zeolite beta was in U.S. Pat. No. 3,308,069 (1967) to Wadinger et al.

J. B. Higgins, et al. of Mobil Research and Development published an article in *Zeolites,* 1988, Vol. 8, November, 446–452 titled "The Framework Topology of Zeolite Beta." In the article Higgins et al. disclose what is known about the framework topology of zeolite beta. The information has been determined using a combination of model building, distance-least-square refinement and powder pattern simulation.

In an article titled "Cumene Disproportionation over Zeolite β I. Comparison of Catalytic Performances and Reaction Mechanisms of Zeolites," *Applied Catalysis,* 77 (1991) 199–207, Tseng-Chang Tsai, Chin-Lan Ay and Ikai Wang disclose a study demonstrating that cumene disproportionation can be applied as a probe reaction for zeolite structure. It is revealed that zeolite beta would have application potential in the production of diisopropylbenzene for reasons of activity, selectivity and stability.

In a second part of the article, "II. Stability Enhancement with Silica Deposition and Steam Pretreatment", Ibid, pp. 209–222, Tsai and Wang disclose their development of two methods to improve the stability of zeolite beta, silica deposition and steam pretreatment.

Patents in the art which employ zeolite beta relate mainly to dewaxing, and cracking of hydrocarbon feedstock.

An article titled "Beta Zeolite as Catalyst or Catalyst Additive for the Production of Olefins During Cracking or Gas Oil," was written by L. Bonetto et al., 9th International Zeolite Conference, July 1992, FP 22. The authors note that with the greater demand for oxygenated compounds there is indication there might be increased demands for catalysts and conditions which maximize $C_3$, $C_4$ and $C_5$ olefins. They suggest that β-zeolite could be used alone or combined with Y-zeolite as a suitable zeolite component. Various catalysts were studied with respect to minimization of diffusional requirements and zeolite stability.

U.S. Pat. No. 4,419,220, to Mobil, discloses a process for dewaxing a hydrocarbon feedstock containing straight chain paraffins which comprises contacting the feedstock with a β-zeolite beta catalyst having a Si:Al ratio of at least 30:1 and a hydrogenation component under isomerization conditions.

Another European Application to Mobil, EP 0 094 827, discloses simultaneous catalytic hydrocracking and hydrodewaxing of hydrocarbon oils with β-zeolite.

In European Patent Application 0 095 303, to Mobil, there is a disclosure of dewaxing distillate fuel oils by the use of β-zeolite catalysts which, preferably have a silica:alumina ratio over 100:1. Ratios as high as 250:1 and 500:1 are disclosed as useful.

Another U.S. Pat. No. 4,518,485, to Mobil, discloses a process for dewaxing a hydrocarbon feedstock containing paraffins selected from the group of normal paraffins and slightly branched paraffins and sulfur and nitrogen compounds where, after conventionally hydrotreating the feedstock to remove sulfur and nitrogen, the hydrotreated feedstock is dewaxed by contacting the feedstock with a catalyst comprising a β-zeolite having a silica/alumina ratio of at least 30:1.

In U.S. Pat. No. 4,740,292, to Mobil, there is disclosed a catalytic cracking process which comprises cracking a hydrocarbon feed in the absence of added hydrogen with a cracking catalyst comprising a β-zeolite component and a faujasite component comprising at least one crystalline aluminosilicate of the faujasite structure, the weight ratio of the faujasite component to the β-zeolite component being from 1:25 to 20:1.

Large pore β-zeolite has been employed in the synthesis of industrially important para-cumene by toluene isopropylation. See "Toluene Isopropylation over Zeolite β and Metallosilicates of MFI Structure," P. A. Parikh et al., *Applied Catalysis, A*, 1992, 90, p. 1.

In European Patent 323138 and U.S. Pat. No. 4,906,787, there is disclosed a catalytic process for converting light olefins to ethers suitable as high octane blending stocks carried out by contacting the olefin, especially propene, with water and alcohol recovered from a downstream distillation operation in an olefin conversion unit in the presence of an acidic zeolite catalyst. In this work diisopropyl ether (DIPE) was prepared from $C_3H_6$ and aqueous iso-PrOH in the presence of silica-bound zeolite Beta catalyst at 166°.

In another European Patent, EP 323268, light olefins are converted to alcohols and/or ethers in the presence of β-zeolite.

In U.S. Pat. No. 5,144,086, to Harandi et al., there is disclosed an integrated multistage process for the production of diisopropyl ether and substantially pure propene wherein in the second stage isopropanol containing about 0%–20% water is contacted with an acidic large pore zeolite etherification catalyst which comprises a β-zeolite having a Si:Al ratio of about 30:1 to 50:1.

Another group of molecular sieve zeolites which have been investigated for industrial application is pentasil zeolites. The pentasil family of zeolites contains a continuing series of which ZSM-5 and ZSM-11 are end members. See T. E. Whyte et al. "Zeolite Advances in the Chemical and Fuel Industries: A Technical Perspective," CATAL. REV.-SCI. ENG., 24, (4), 567–598 (1982).

A good overview of applications for zeolites, including pentasil type zeolites is found in an article titled, "Zeolite Catalysts Face Strong Industrial Future", European Chemical News, Jul. 10, 1989, p. 23. For example, medium pore H-ZSM-5 is sometimes added to a zeolite Y catalytic cracking catalyst to increase the aromatics content and hence motor octane, of the gasoline fraction. In the limited space of ZSM-5, where two pore systems of about 5–6Å in diameter intersect to give spatial regions of around 9Å diameter at the intersections, there is a cutoff around $C_{10}$ to $C_{11}$ for products from transformation of a wide range of feedstocks, including alkanes, olefins and alcohols.

The Pentasil ZSM-5 is a catalyst used for converting methanol to gasoline, processing C-8 streams, selectively isomerizing m-cresol to p-cresol, suppressing the formation of diphenylalanine in the production of aniline, and producing pyridine and β-picoline from acetaldehyde, formaldehyde and ammonia.

In an Article titled "Shape Selective Reactions with Zeolite Catalysts", J. CATAL., 76, 418 (1982), L. B. Young et al. report data on selectivity in xylene isomerization, toluene-methanol alkylation, and toluene disproportionation over ZSM-5 zeolite catalysts. Some of the ZSM-5 zeolites in this study were modified. It was demonstrated that appropriately modified ZSM-5 class zeolites are capable of generating uniquely selective compositions. Intrinsic reactivities and selectivities are considerably altered with these modified catalysts.

There is a discussion of the shape selective properties of ZSM-5 in "A Novel Effect of Shape Selectivity: Molecular Traffic Control In Zeolite ZSM-5", by E. G. Derouane, et al., J. CATAL., 65, 486 (1980). Some of the observations included the following: (i) linear aliphatics diffuse rather freely in the ZSM-5 framework and can be adsorbed in both channel systems; (ii) isoaliphatic compounds experience stearic hinderance which may restrict their diffusion in the sinusoidal channel system; and (iii) aromatic compounds and methyl substituted aliphatics have a strong preference for diffusion and/or adsorption in the linear and elliptical channels.

E. G. Derouane et al. studied shape selective effects in the conversion of methanol to higher hydrocarbons and alkylation of p-xylene on pentasil-family zeolites. Some of these zeolites were modified by the incorporation of phosphorous, or embedded in a silica filler. Their findings are reported in "Molecular Shape Selectivity of ZSM-5, Modified ZSM-5 and ZSM-11 Type Zeolites", in FARADAY DISCUSSIONS, 72, 331 (1981).

P. Chu et al. report results of one study in "Preparation of Methyl tert-Butyl Ether (MTBE) over Zeolite Catalysts", IND. ENG. CHEM. RES., 26, 365 (1987). They reported that ZSM-5 and ZSM-11 have been identified to be highly selective zeolite catalysts for the preparation of MTBE from isobutylene.

Another reference which discusses the use of pentasil zeolites in MTBE service is by G. H. Hutchings, et al., CATAL. TODAY, 15, 23 (1992).

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

Japanese Patent 82-07432 teaches the use of zeolites, particularly mordenites and faujasites, to make dialkyl ethers containing primary or secondary alkyl groups by the liquid phase dehydration of alcohols.

In allowed U.S. patent application Ser. No. 07/917,218, there is disclosed a method for preparing methyl tertiary butyl ether by reacting butanol and methanol in the presence of a catalyst comprising a super-acid alumina or a faujasite-type zeolite.

In U.S. Pat. No. 5,081,318, a Y-type zeolite modified with fluorosulfonic acid is disclosed.

In U.S. Pat. No. 5,208,387, also to Harandi et al., there is disclosed a process for the acid catalyzed production of DIPE from propene and water feed stream that eliminates the propene recycle stream to the olefin hydration reactor and achieves high propene conversion. This process is carried out in two stages wherein the first stage comprises a zeolite catalyzed hydration and etherification of propene employing a minimum of water feed and the second stage converts unconverted propene from the first stage reactor by hydration and etherification to DIPE.

In an article titled "Race to License New MTBE and TAME Routes Heats Up", Rotman, D., *Chemical Week*, Jan. 6, 1993, p. 48, there is a review of new technology at several different companies which centers around skeletal isomerization, particularly of $C_4$ and $C_5$ olefins. The interest in this technology is fueled by the promise of dramatically increased and relatively inexpensive isobutylene and isoamylene that could boost MTBE and TAME production, often constrained by the amounts of available isobutylene in refinery or steam cracker streams. DIPE production from propylene is also discussed.

Mobil Corp. has disclosed new etherification technology that can produce fuel oxygenates based only on olefinic refinery streams and water. This process has the potential to allow refiners to produce oxygenates without having to rely on an external supply of alcohols. The technology is developed around diisopropyl ether (DIPE) based on propylene. The DIPE has similar physical and blending activities to MTBE and TAME and is a perfectly acceptable fuel oxygen source. Wood, A., *Chemical Week*, Apr. 15, 1992, p. 7.

None of the available references would seem to suggest the one-step conversion of low value crude acetone in a by-product stream into useful oxygenate products. The portion of said by-product stream which typically comprises acetone is about 20% to 80%. It would greatly enhance the economics of any process to produce MTBE or other oxygenates if acetone from a by-product stream could be converted in one step to useful oxygenate products which could be fractionated to isolate diisopropyl ether (DIPE) and isopropyl tertiary butyl ether (IPTBE).

SUMMARY OF THE INVENTION

In accordance with the foregoing, the novel method of the instant invention for the generation of diisopropyl ether and isopropyl t-butyl ether in one step from a crude by-product acetone stream comprises reacting an acetone-rich feed over a bifunctional catalyst comprising 5%–45% by weight hydrogenation catalyst consisting essentially of one or more metals from the group consisting of nickel, copper, platinum, palladium, tin and chromium supported on a dehydration/etherification catalyst comprising 55% to 95% by weight of the bifunctional catalyst. The etherification catalyst comprises a support consisting essentially of 5% to 95% by weight zeolite from the group consisting of β-zeolite, pentasil zeolite and Y-zeolite and 95% to 5% by weight of a metal oxide selected from Group III or IV of the Periodic Table.

DETAILED DESCRIPTION OF THE PREFERRED EMBODIMENT

Figure 2:
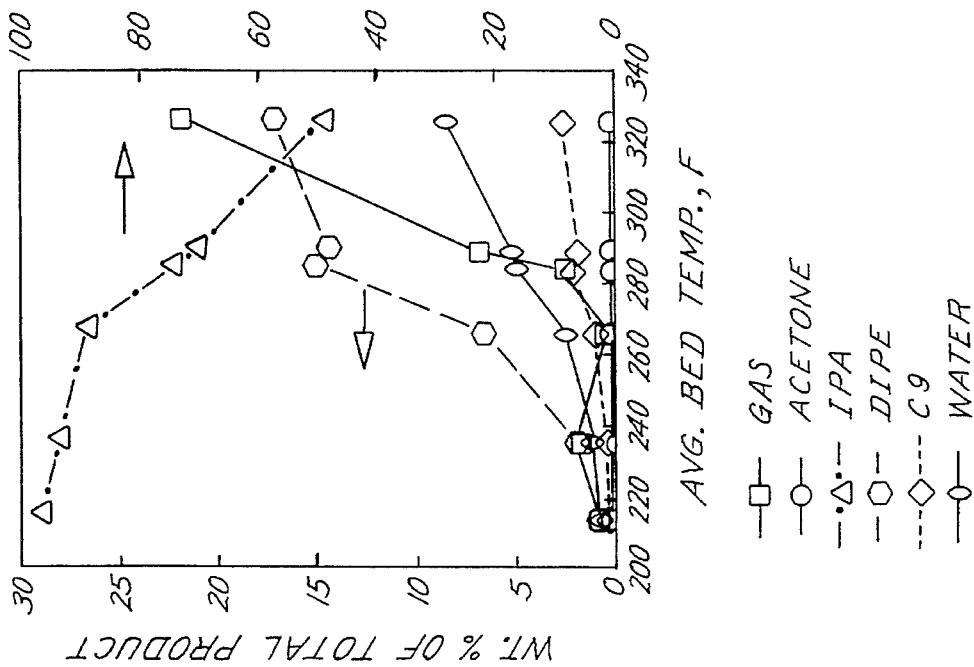
FIG. 2 represents the product distributions as a function of temperature for the catalyst containing nickel and copper on 10% β-zeolite and 90 wt. % alumina.
Figure 1:
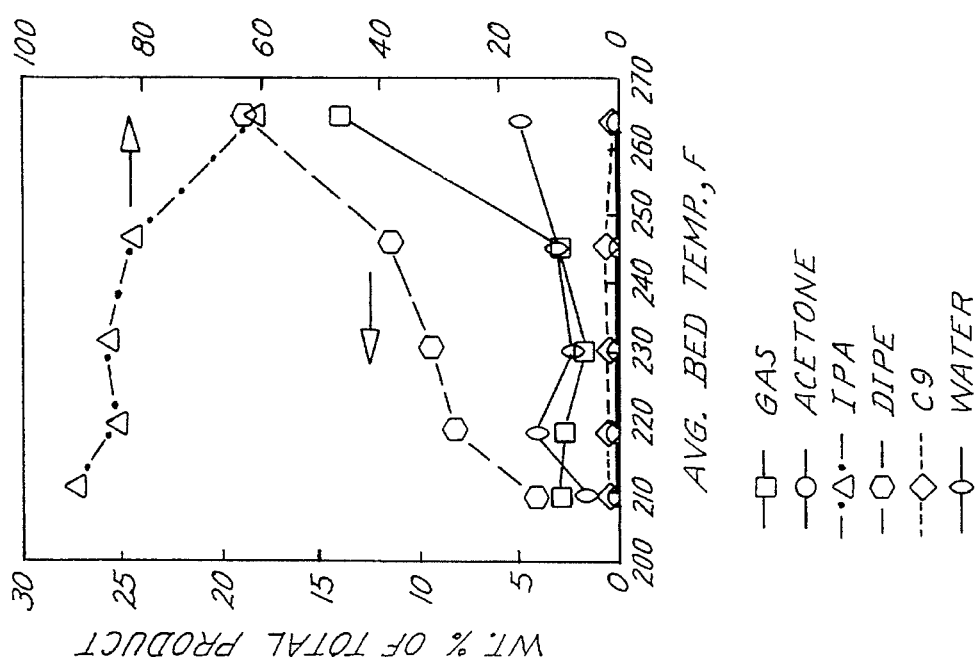
FIG. 1 represents the product distribution as a function of temperature for the catalyst containing nickel and copper on 50 wt. % β-zeolite and 50 wt. % alumina.

In the production of high octane blending components for reformulated gasoline such as diisopropyl ether (DIPE), methyl t-butyl ether (MTBE) and isopropyl t-butyl ether (IPTBE) by the method outlined above, the by-product acetone stream contains, in addition significant quantities, that is, preferably greater than 5% of both methanol (MeOH) and t-butanol (tBA). For the cogeneration of DIPE, MTBE and IPTBE, the crude acetone feed preferably contains 10%–40% each of both methanol and t-butanol.

The one-step synthesis can be represented by:

In a process to make propylene oxide a large number of by-products are typically generated with the desired product. The by-products may include formic acid, acetic acid, t-butanol and acetone. The acetone may constitute about 20% to 80% of certain crude by-product streams. These crude acetone streams may be further mixed with methanol.

In related art, it is known to produce IPA and DIPE by the hydration of propylene and subsequent etherification of IPA. The instant invention allows the production of IPA and DIPE as well as other ethers such as MTBE and IPTBE from crude acetone containing tBA and MeOH in one-step in the presence of a bifunctional catalyst and hydrogen. The bifunctional catalyst comprises 5%–45% by weight hydrogenation catalyst consisting essentially of one or more metals from the group consisting of nickel, copper, platinum, palladium, tin and copper on 55% to 95% of the total catalyst weight of a support consisting essentially of a zeolite and an oxide of Group III or IV of the Periodic Table.

The total percent by weight of the portion of the catalyst comprising a hydrogenation catalyst is preferably between 5 wt. % and 40 wt. % The hydrogenation portion of the catalyst may comprise one or more metals selected from the group consisting of platinum, palladium, nickel, copper, tin and chromium. A preferred combination is nickel and copper, where the total metal content of Ni/Cu is in the range of 8 wt. % to 40 wt. % and preferably 25% to 35%. The catalyst contains a nominal loading of nickel between 20 wt. % and 30 wt. %, preferably 15%–30% and particularly about 28%, and a nominal loading of copper of 2 wt. % to 15 wt. %, preferably about 4%.

In some cases it is useful to include chromium with nickel and copper, as demonstrated in Example 4. When employed, an amount of about 1 wt. % to 5 wt. % is appropriate, preferably about 2 wt. %.

The etherification portion of the catalyst preferably comprises 5%–95% by weight of β-zeolite or medium-pore pentasil zeolite and 95%–5% of an oxide of Group III or IV. With respect to the etherification portion of the catalyst, the zeolite preferably comprises 5% to 65% by weight and the metal oxide comprises 95% to 45% by weight. Example 1 demonstrates the use of a Ni-Cu hydrogenation catalyst on a support comprising 10% by weight β-zeolite and 90% alumina, while Example 2 demonstrates 50% β-zeolite and 50% alumina.

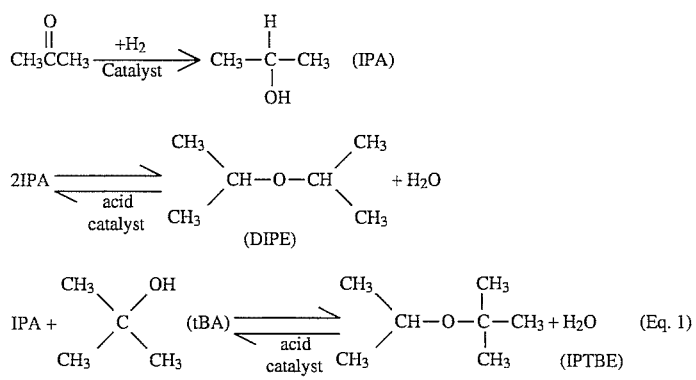

(Eq. 1)

It appears that the zeolites which are most useful for the etherification portion of the bifunctional catalyst are large pore zeolites, such as, for example, β-zeolite or medium pore pentasil zeolites, i.e., those having a pore size of greater than about 5.5Å.

The composition of zeolite beta is described in U.S. Pat. Nos. 3,308,069; 4,419,220; 4,518,485 and 4,740,292. In those references, zeolite beta is typically described as follows:

Zeolite beta is a crystalline aluminosilicate having a pore size greater than 5 Angstroms. The composition of the zeolite, as described in U.S. Pat. No. 3,308,069, in its as synthesized form may be expressed as follows:

[XNa(1.0±0.1−X)TEA]AlO$_2$·YSiO$_2$·WH$_2$O where X is less than 1, preferably less than 0.7; TEA represents the tetraethylammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analyzed value of sodium and the theoretical cation to structural aluminum ratio of unity.

As discussed in the J. B. Higgins, et al. reference, supra, p. 446, the first clues to the crystal structure of zeolite beta were evidenced from chemical and physical property measurements. Ion-exchange isotherms of Na-β at 25° C. indicated that cations as large as tetraethylammonium (TEA$^+$) exchanged completely into the pore system. This behavior suggests that beta contains at least 12-membered rings opening into channels, because TEA$^+$ is too large to exchange through 10-membered rings such as those in ZSM-5. The complete exchange of cations in beta indicated the presence of channels instead of cages, because it is not possible to remove all the cations from cage structures such as Na faujasite. Additional evidence was obtained from organic sorption data and density measurements. Cyclohexane sorption of 14.6–19.4 wt. % and a measured density of 1.61 g/cm$^3$ ruled out undimensional pore systems such as those in ZSM-12, ZSM-22, ZSM-23 and ZSM-48. Structural similarities among beta, mordenite and ZSM-12 were suspected because all three may be synthesized in Na$^+$-TEA$^+$ systems from highly siliceous batch compositions. Further, zeolite beta is easily synthesized in the SiO$_2$/Al$_2$O$_3$ range of 30–50. This lies between TEA$^+$ mordenite (typically 10–30) and ZSM-12 (typically, >60), suggesting the beta framework contains large fractions of both 4- and 5-membered rings.

In the Tsai and Wang reference, supra, part II, p. 209, stability enhancement is discussed. Two methods, silica deposition and steam pretreatment, have been developed to substantially improve zeolite beta stability.

Ibid, p. 215, it is stated that zeolite beta has two types of three dimensional pore openings, the linear and the tortuous channel. The former has pore openings of 7.5Å×5.7Å and the latter has pore openings of 6.5Å×5.6Å. When silica, for example, is deposited on zeolite beta, the pore opening was narrowed or blocked by the deposited silica. It was concluded that silica deposition selectively removes strong acid sites and increases the population of medium acid sites.

In the fully base-exchanged form, zeolite beta has the composition:

[(X/n)M(1±0.1−X)H]AlO$_2$·YSiO$_2$·WH$_2$O where X, Y and W have the values listed above and n is the valence of the metal M. This form of the zeolite may be converted partly to the hydrogen form by calcination, e.g. at 200° C. to 900° C. or higher. The completely hydrogen form may be made by ammonium exchange followed by calcination in air or an inert atmosphere such as nitrogen, see U.S. Pat. No. 4,419,220.

Zeolite beta is characterized by the following X-ray diffraction pattern:
d Values of Reflection in zeolite beta
11.40±0.2
7.40±0.2
6.70±0.2
4.25±0.1
3.97±0.1
3.00±0.1
2.20±0.1

The preferred forms of zeolite beta are the highly acidic, high silica forms, having silica-to-alumina mole ratio of at least 10:1, and preferably in the range of 10:1 to 50:1 in the as-synthesized form, and a surface area of at least 100 m$^2$/g.

Suitable β-zeolites for the practice of this invention include Valfor C806β, Valfor CP815β and Valfor C861. Valfor® is the registered trademark of the PQ Corporation. Valfor® C806β zeolite is zeolite beta powder in template cation form. It is a high silica shape selective zeolite which contains the organic template used in the crystallization step, having been isolated after filtration and washing of the synthesis product. C806β has a SiO$_2$/Al$_2$O$_3$ molar ratio of 23–26; the crystal size is 0.1–0.7 um; the surface area after calcination is about 700–750 m$^2$/g; the cyclohexane adsorption capacity after calcination is 19–24 g/100 g; Na$_2$O content is about 0.01–1.0% by weight anhydrous; and, the organic content is about 11–13% by weight, on a water-free basis.

Valfor® C815β zeolite is a calcined zeolite beta powder in hydrogen, sodium form. It is similar to C806β except the product has been calcined to decompose the organic template. C815β is a high silica, shape selective aluminosilicate with a large pore diameter. C815β also has a SiO$_2$/Al$_2$O$_3$ molar ratio of about 23–26; the crystal size, surface area, cyclohexane adsorption capacity and Na$_2$O are all within the same ranges as given for C806β.

Also, very effective in the bifunctional catalyst were the isostructural group of medium-pore pentasil zeolites.

An article titled "Molecular Sieve Catalysts," by J. Ward, Applied Industrial Catalysis, Vol. 3, Ch. 9, p. 271 (1984) provides an overview of the structure of pentasils. These zeolites, as well as silicalite have SiO$_2$-Al$_2$O ratios greater than 10. Silicalite is an inorganic molecular sieve described in U.S. Pat. No. 4,061,724, incorporated herein by reference in its entirety. Silicalite usually has a Si:Al ratio greater than 200. Silicalite, ZSM-5, ZSM-11 and related materials have structures with ten-ring channel systems in contrast with the eight-membered zeolites such as A and erionite and the twelve-membered systems such as zeolites X and Y.

Pentasil zeolites are hydrophobic compared with A, X and Y zeolites. ZSM-5 has orthorhombic unit cells, whereas ZSM-11 is tetragonal.

The pentasil structures are very thermal and acid stable. They are synthesized in the presence of ammonium ions, which become an integral part of the structure. Heating up to 600° C. decomposes the organic cations leaving the highly porous structure.

The channel size of pentasil materials is intermediate between, for example, small pore erionite and large pore zeolite Y.

Other ZSM series zeolites are not considered to be pentasils. ZSM-21, ZSM-35 and ZSM-38 are considered to be of the ferrierite type zeolite. ZSM-20 is considered of the faujasite type and ZSM-34 is considered to be of the offretite/erionite group. Whyte, supra, p. 571.

Medium pore, pentasil-type zeolites having 10-membered oxygen ring systems include, for example, ZSM-5, ZSM-11, ZSM-22, ZSM-23, ZSM-48 and laumontite. Their framework structures contain 5-membered oxygen rings and they are more siliceous than previously known zeolites. In many instances these zeolites may be synthesized with a predominance of silicon and with only a very small concentration of other atoms such as aluminum; thus, these zeolites may be considered as "silicates" with framework substitution by small quantities of other elements such as aluminum. Among the zeolites in this group, only ZSM-5 and ZSM-11 have bidirectional intersecting channels, the others have nonintersecting unidirectional channels.

The medium-pore pentasils, unlike other zeolites, have pores of uniform dimension and have no large supercages with smaller size windows. This particular feature is believed to account for their unusually low coke-forming propensity in acid-catalyzed reactions. Because the pentasil zeolites are devoid of the bottle-necks in the window/cage structure, molecules larger than the size of the channel do not form with the exception perhaps at the intersections.

The preferred forms of pentasil zeolite are the highly acidic, high silica forms, having silica-to-alumina mole ratio of at least 30:1, and preferably in the range of 30:1 to 350:1 in the as-synthesized form. A narrower range of 50:1 to 150:1 is preferred and the pentasil zeolites demonstrated in the examples possess $SiO_2/Al_2O_3$ ratios of about 31:1 to ca. 350:1.

Said zeolite etherification catalysts are formed in the presence of a binder, such as Group III or Group IV oxide. The zeolites are combined with the binder by a variety of forming techniques. Group IV oxides used in conjunction with said β-zeolite include oxides of aluminum, silicon, titanium, zirconium, hafnium, germanium, tin and lead, as well as combinations thereof. Alumina is preferred. Said binders may comprise as much as 10% to 90% of the formed catalyst.

Said metal oxide may optionally be further modified with a halogen, a halogen-containing organic compound, or a halogen-containing acid. Said halogen may be fluorine, chlorine, bromine or iodine, but is preferably fluorine. In the case of fluoride treatment, the fluoride content of the treated β-zeolite may be in the range of 0.1 to 10 wt. %, but preferably is about 1%. Said fluoride-treated zeolites may optionally be calcined, at temperatures of 200° C. and above, prior to further usage or modification.

Another type of zeolite which should be useful in the etherification portion of this integrated catalyst generally comprises dealuminated Y-zeolite catalysts.

The zeolites to use in the dealuminated form for the reaction of Eq. 1 are certain crystalline aluminosilicate zeolites, particularly the isostructural group of faujasite zeolites that include the synthetic X- and Y-zeolites, of which the Y-zeolites are preferred.

The unit cells of faujasite zeolites are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$$Na_{56}[(AlO_2)_{56}(SiO_2)_{136}]x \cdot 250\ H_2O$$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48, resulting in a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms (designated T atoms) taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The α-cage is a 26-hedron with a free diameter of ≈1.3 nm, and it can be entered through four distorted 12-member rings of diameter 0.80–0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol. % of the dehydrated crystal. From the catalytic viewpoint, the α-cages are by far the most important, since, unlike the β-cages, they permit entry of numerous aliphatic and aromatic compounds.

Preferably, said Y-zeolites are dealuminated by ammonium exchange followed by calcination, or by treatment with ethylenediaminetetraacetic acid (EDTA) or other chelating agents or by treatment with fluorine or a fluorine-containing compound such as silicon tetrafluoride or ammonium fluorosilicate, or hydrothermal treatment and/or acid treatment. Said dealuminated Y-zeolites should have a silica-to-alumina molar ratio of greater than three, preferably a ratio of 5 or greater and most preferably a silica-to-alumina ratio of 5 to 100. The examples demonstrate the usefulness of catalysts having a silica-to-alumina ratio of 5 to 50 and particularly 15 to 30.

Examples of suitable commercially available dealuminized Y-zeolites include UOP's LZY-82 and LZY-72, PQ Corporation's CP-304-37 and CP-316-26, UOP's Y-85, Y-84, LZ-10 and LZ-210.

The unit cell size and $SiO_2/Al_2O_3$ molar ratio for typical dealuminated Y-zeolites are noted in the following table:

| ZEOLITE TYPE | UNIT CELL SIZE, A | $SiO_2/Al_2O_3$ MOLAR |
|---|---|---|
| LZY-82 | 24.53 | 7.8 |
| LZY-85 | 24.49 | 9.1 |
| LZY-10 | 24.32 | 23.7 |
| LZY-20 | 24.35 | 18.9 |
| LZY-84 | 24.51 | 8.4 |
| LZ-210 | 24.47 | 9.9 |
| LZY-72 | 24.52 | 8.1 |
| CP316-26 | 24.26 | 45.7 |

Particularly effective in the subject cogeneration of MTBE, IPTBE and DIPE are the β-zeolites containing metal oxide carriers.

Said catalysts may be in the form of powders, pellets, granules, spheres, shapes and extrudates. The examples described herein demonstrate the advantages of using extrudates.

The reaction may be carried out in either a stirred slurry reactor or in a fixed bed continuous flow reactor. The catalyst concentration should be sufficient to provide the desired catalytic effect.

Dehydration/etherification to DIPE, MTBE or ITPBE can generally be conducted at temperatures from 20° to 250° C.; the preferred range is 50° to 200° C. Good results are observed throughout this temperature range. However, it can be noted that the best conversion figures for MTBE, DIPE cogeneration are observed when the temperature is 210°–290° F. (99°–143° C.). The total operating pressure may be from 0 to 5000 psig, or higher. The preferred pressure range is 100 to 1000 psi.

Typically, IPA and DIPE are generated continuously in up to ca. 98 wt. % concentration or greater in the crude liquid product at total liquid hourly space velocities (LHSV) of up to 10 or higher and relatively mild conditions, where:

$$LHSV = \frac{\text{Volume of Total Liquid Feed Run Through The Reactor Per Hour}}{\text{Volume of Catalyst In Reactor}}$$

Conversions of acetone are estimated in the following examples using the equation:

$$\frac{(\text{Mole \% of Acetone in Feed} - \text{Mole \% of Acetone in Product})}{\text{Mole \% of Acetone in Feed}} \times 100$$

In the examples which follow it is noted that:

Acetone is almost completely converted to IPA (major product) as well as small amounts of 2-methyl pentane and unknown alcohol.

In Example 1, optimum selectivity to DIPE (15.4%–15.9%) was achieved at the reaction temperature of about 284°–289° F. Temperatures greater than 290° F. appear to be detrimental to the combined yields of the desired products (IPA+DIPE) and tends to promote the dehydration reaction of IPA to propylene, leading to the formation of large amounts of gas products.

In Example 2, over the temperature range of 210°–264° F., the DIPE yield increases with increasing temperature.

A comparison between Example 2 and Example 1 for the DIPE yields at each comparable temperature indicates that the higher the β-zeolite content, the greater the DIPE yield. Up to 20% of selectivity to DIPE was attained in Example 2 at 264° F. The combined yields of IPA and DIPE reaches a maximum value of 96.2% at 246° F.

The results clearly demonstrate that high yield of IPA and DIPE can be generated from the hydrogenation of pure acetone over one NiCu catalyst on a β-zeolite/alumina support. The total metal content of Ni+Cu is in the range of 8 wt. % to 40 wt. %, and the atomic ratio of Ni/Cu is in the range of 1:1 to 10:1. The β-zeolite content in the support ranges from 5%–95%.

The following examples are merely illustrative of the preferred embodiment. Many variations thereon may be made without departing from the spirit of the disclosed invention, as will be evident to those skilled in the art.

EXAMPLE 1

A 32% NiCu on 10% Beta catalyst was prepared impregnating a support containing 50 g of 10% β-zeolite/90% alumina support with a 40 cc aqueous solution containing 51 g of nickel nitrate hexahydrate and 5.4 grams of copper nitrate hemipentahydrate. The impregnated support was dried at 250° F. for 2 hours and then calcined at 600° F. for 4 hours. The calcined support was impregnated again with a 37 cc aqueous solution containing 51 g of nickel nitrate hexahydrate and 5.4 g of copper nitrate hemipentahydrate. The impregnated support was dried at 250° F. for 2 hours and then calcined at 900° F. for 8 hours. The finished catalyst is coded as 052-92-6888-036.

Catalyst screening runs were performed in a microreactor test unit which has two reactors in series separated by a quench zone. The reactors were operated in a downflow configuration. The top reactor was loaded with a 4 cc catalyst. The second reactor has two catalyst beds of 4 cc of catalyst each separated by a 4 cc bed of inert material. The total charge of catalyst was 12 cc in the unit. Internal thermocouples were positioned at the bottom of each catalyst bed. The liquid feed was charged to the unit using a high pressure pump and the hydrogen was metered through a mass flow controller. Both hydrogen and liquid feedstock were mixed and charged to the unit. The molar ratio of hydrogen to acetone is about 0.5:1 to 30:1, preferably about 1:1 to 3:1. For the purpose of simplifying the analysis of liquid products by GC, technical grade acetone (97% purity) was used as a feedstock to demonstrate the chemistry involved in the instant invention.

The catalyst, Example 1, was activated by heating slowly from room temperature to 600° F. over an 8 hour period under flowing nitrogen at 70 psig. The unit pressure was then raised to 500 psig with hydrogen and the catalyst bed was held at 600° F. for 12 hours under flowing hydrogen. The catalyst bed was cooled down to below 200° F. The technical grade acetone (97% purity) was charged to the unit at 1 LHSV and 500 psig. The hydrogen flow rate was controlled to give a hydrogen to acetone mole ratio of 5:1. The reaction temperature was varied from 210° F. to 325° F. The liquid product was collected periodically in a chilled receiver at 0° F. and 300 psig. The product was analyzed by GC to determine the composition of hydrocarbon and oxygenates, and by Karl-Fischer titration for the water content.

The results of the analysis of liquid products are summarized in Table 1.

TABLE I

Run No. 097-93-6005
Catalyst: 052-92-6888-036 32% NiCu on 10% Beta Support

| Cut No. | TOS Hr. | Avg. Temp. | Liquid Recov. wt % | C3 wt % | Acetone wt % | IPA wt % | DIPE wt % | C6/C9 wt % | Water wt % |
|---|---|---|---|---|---|---|---|---|---|
| 040 | 17 | 214 | 99 | 0.9 | 0 | 97.4 | 0.5 | 0.5 | 0.9 |
| 070 | 23 | 235 | 98 | 1.8 | 0 | 94.6 | 1.9 | 0.5 | 1.1 |
| 090 | 29 | 266 | 100 | 0.5 | 0.1 | 89.6 | 6.6 | 0.9 | 2.4 |
| 110 | 35 | 289 | 93 | 6.8 | 0.1 | 71.4 | 14.6 | 1.8 | 5.1 |
| 130 | 41 | 284 | 98 | 2.5 | 0.1 | 75.1 | 15.1 | 2.5 | 4.8 |
| 150 | 47 | 290 | 82 | 18.8 | 0.2 | 64.6 | 8.2 | 3.6 | 4.6 |
| 170 | 53 | 325 | 80 | 22.1 | 0.2 | 49.2 | 17.2 | 2.6 | 8.6 |

EXAMPLE 2

The catalyst of Example 2 was prepared by following the same procedures as described above for Example 1 except the support is a mixture of 50% β-zeolite and 50% alumina. The finished catalyst is coded as 052-92-6888-047.

The catalyst was activated and technical grade acetone was charged in the same manner as used in Example 1.

The result of the analysis of liquid products are summarized in Table II. The product distributions as a function of reaction temperature are represented in FIG. 2.

The catalyst was activated and tested in the same manner as used in Example 1. The result of the analysis of liquid products are summarized in Table III.

The results show that as the reaction temperature approached 256° F., up to 25 wt. % of selectivity to DIPE was attained, and the combined yields of IPA and DIPE was 89.8 wt. %.

TABLE II

Run No. 097-93-6006
Catalyst: 052-92-6888-042 32% NiCu on 50% Beta support

| Cut No. | TOS Hr. | Avg. Temp. | Liquid Recov. wt % | C3 wt % | Acetone wt % | IPA wt % | DIPE wt % | C6/C9 wt % | Water wt % |
|---|---|---|---|---|---|---|---|---|---|
| 160 | 44 | 210 | 97 | 2.9 | 0 | 91.0 | 4.0 | 0.4 | 1.6 |
| 180 | 48 | 219 | 99 | 2.8 | 0 | 84.3 | 8.2 | 0.5 | 4.1 |
| 200 | 52 | 231 | 99 | 1.8 | 0 | 86.0 | 9.3 | 0.5 | 2.4 |
| 220 | 55 | 246 | 97 | 2.9 | 0.1 | 81.7 | 11.5 | 0.6 | 3.1 |
| 240 | 60 | 264 | 86 | 14.1 | 0.1 | 61.1 | 19.0 | 0.4 | 5.0 |

EXAMPLE 3

The catalyst of Example 3 was prepared by following the same procedures as described above for Example 1 except the support is a mixture of 60% β-zeolite and 40% alumina. The finished catalyst is coded as 052-93-6896-021.

TABLE III

Catalyst: 052-93-6896-021 32% NiCu on 60% Beta Support

| Cut No. | TOS Hr. | Avg. Temp. | Liquid Recov. wt % | C3 wt % | Acetone wt % | IPA wt % | DIPE wt % | C6/C9 wt % | Water wt % |
|---|---|---|---|---|---|---|---|---|---|
| Run No. 097-93-6016 | | | | | | | | | |
| 600 | 10 | 205 | 100 | 0 | 0 | 91.5 | 4.6 | 1.5 | 2.4 |
| Run No. 097-93-6017 | | | | | | | | | |
| 600 | 4 | 239 | 100 | 0 | 0 | 90.4 | 5.4 | 1.5 | 2.6 |
| 700 | 8 | 260 | 100 | 0.3 | 0 | 63.2 | 20.7 | 1.0 | 14.9 |
| Run No. 097-93-6018 | | | | | | | | | |
| 500 | 7 | 256 | 100 | 0.3 | 0 | 65.0 | 24.8 | 1.8 | 7.9 |

EXAMPLE 4

The catalyst of Example 4 is used to illustrate the application of a medium-pore pentasil zeolite, ZSM-5, in this process. The catalyst was prepared by using a support (8162CT91) comprising a 80 wt. % of ZSM-5 zeolite having a silica/alumina mole ratio of 223 and 20 wt. % of alumina. 50 grams of the dried support was impregnated with 35 cc solution containing 11.4 grams of copper nitrate, 2.2 grams of nickel nitrate and 4.4 grams of chromium nitrate. The impregnated support was dried at 250° F./2 hours and calcined at 600° F./2 hours and 800° F./4 hours. The resulting catalyst, coded as 052-92-6888-040, contains 7 wt. % CuO, 2 wt. % $CrO_3$, and 1 wt. % NiO.

The catalyst was activated and tested in the same manner as used in Example 1. The result of the analysis of liquid products are summarized in Table IV. The results show that at 219° F. the combined yields of IPA and DIPE of 92.5 wt. % and about 10 wt. % DIPE were obtained using a ZSM-5 zeolite-containing catalyst.

TABLE IV

Run No. 097-93-6026
Catalyst: 052-92-6888-040 CuCrNi on 80% Silicalite Support

| Cut No. | TOS Hr. | Avg. Temp. | Liquid Recov. wt % | C3 wt % | Acetone wt % | IPA wt % | DIPE wt % | C6/C9 wt % | Water wt % |
|---|---|---|---|---|---|---|---|---|---|
| 100 | 10 | 219 | 100 | 1.8 | 0 | 82.7 | 9.8 | 1.3 | 4.5 |

What is claimed is:

1. A one-step integrated process for generation of ethers from a crude by-product acetone stream which comprises reacting said acetone stream with hydrogen over a single bifunctional catalyst comprising: 5%–45% by weight of one or more metals from the group consisting of Group IB and Group VIII on a support comprising 55% to 95% by weight of the total catalyst of a support selected from the group consisting of β-zeolite, dealuminated Y-zeolite and pentasil zeolites optionally mixed with a metal oxide selected from Group III or IV of the Periodic Table.

2. The method of claim 1 wherein the β-zeolite content in the catalyst support ranges from 5% by weight to 95% by weight.

3. The method of claim 1 wherein the β-zeolite content in the support ranges from 45% to 85%.

4. The method of claim 1 wherein the β-zeolite content in the support ranges from 5% to 15%.

5. The method of claim 1 wherein the medium-pore pentasil zeolite is ZSM-5 having a silica to alumina mole ratio of 30–350.

6. The method of claim 5 wherein the zeolite content of the etherification catalyst ranges from 65% to 80%.

7. The method of claim 1 wherein the hydrogenation catalyst consists essentially of nickel and copper.

8. The method of claim 7 wherein the metal content of the hydrogenation catalyst comprises 25%–35% by weight of the total weight of the catalyst, wherein 15%–30% is nickel and 2%–15% is copper.

9. The method of claim 8 wherein the hydrogenation portion of the catalyst also includes 1 wt. % to 5 wt. % chromium.

10. The method of claim 1 wherein the catalyst support comprises 5% to 95% by weight metal oxide selected from Group III or IV of the Periodic Table.

11. The method of claim 10 wherein the Group III or IV oxide support is selected from the group consisting of alumina or silica alumina.

12. The method of claim 11 wherein the oxide is treated with fluoride.

13. The method of claim 1 wherein the temperature ranges from 50° C. to 200° C.

14. The method of claim 1 wherein the hydrogen pressure is about 100 psig to 1000 psig.

15. The method of claim 1 wherein the liquid hourly space velocity ranges from about 0.1–10/hr.

* * * * *